United States Patent [19]  [11] 4,209,510
Spielvogel et al.  [45] Jun. 24, 1980

[54] AMMONIA-CYANOBORANE, SODIUM IODIDE COMPLEX

[75] Inventors: Bernard F. Spielvogel; Andrew T. Mc Phail, both of Durham; Iris H. Hall, Chapel Hill, all of N.C.; Patty Wisian-Neilson, Fort Worth, Tex.; Karl D. Hargrave, Durham, N.C.

[73] Assignee: The United States of America as represented by the Secretary of the Army, Washington, D.C.

[21] Appl. No.: 960,700

[22] Filed: Nov. 14, 1978

[51] Int. Cl.$^2$ ............... C01B 35/06; A61K 33/18; A61K 33/22
[52] U.S. Cl. .................................. 424/148; 423/284
[58] Field of Search ..................... 423/284; 424/148

[56] References Cited

U.S. PATENT DOCUMENTS 3,667,923  6/1972  Wade ................................. 423/284

OTHER PUBLICATIONS

Bratt, P. J. et al., "J.C.S. Dalton", 1976, pp. 353–356.

Primary Examiner—G. O. Peters
Attorney, Agent, or Firm—William G. Gapcynski; Sherman D. Winters; Werten F. W. Bellamy

[57] ABSTRACT

Preparation of the crystalline complex [Na{NH$_3$.BH$_2$(CN)}$_6$]I from NMe$_3$.BH$_2$I and NaCN in liquid NH$_3$ is disclosed. Structural details of this novel octahedral complex are obtained by single-crystal X-ray analysis. Evidence indicates that the complex is a valuable antiarthritic agent, since it completely inhibits bacteria-induced chronic arthritis in rats with no evidence of toxic effects. The complex also possesses analgesic and anti-inflammatory activity.

5 Claims, 2 Drawing Figures

AMMONIA-CYANOBORANE, SODIUM IODIDE COMPLEX

BACKGROUND OF THE INVENTION

Several adducts of cyanoborane have been reported in the chemical literature. See B. F. Spielvogel et al, *Abs. Southeast Regional Meeting*, American Chemical Society, Richmond, Virginia, November 1969; *Chem. Eng. News*, 1969, vol. 33, p. 36; S. S. Uppal et al, *Chem. Comm.*, 1970, p. 1619; C. Weidig et al, *Inorg. Chem.*, 1974, vol. 13, p. 1763; B. F. Spielvogel et al, *J. Amer. Chem. Soc.*, 1972, vol. 94, p. 8597; P. J. Bratt et al, *J. C. S. Dalton*, 1974, p. 2161. However, there has been only one report of the synthesis of ammonia-cyanoborane. See P. J. Bratt et al, *J. C. S. Dalton*, 1976, p. 353. We have now successfully prepared a novel octahedral complex which we have identified as [Na{NH$_3$.BH$_2$(CN)}$_6$]I. Evidence indicates that this new complex is a valuable antiarthritic agent. The complex also possesses analgesic and anti-inflammatory activity.

Also note that the preparation and X-ray analysis of the complex of this invention was reported by Hargrave et al, *J. C. S. Dalton*, 1977, 2150–53.

BRIEF DESCRIPTION OF THE DRAWINGS

Referring to the drawings.

DETAILED DESCRIPTION OF THE INVENTION

EXPERIMENTAL

Figure 1:
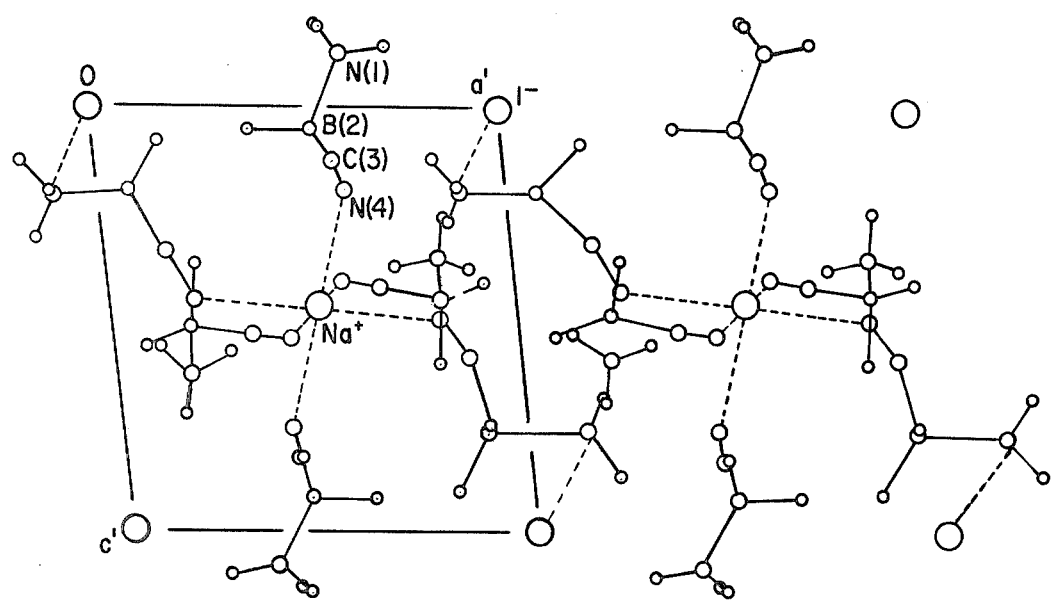
FIG. 1 depicts the atom-numbering scheme and crystal structure of [Na{NH$_3$.BH$_2$(CN)}$_6$]I viewed in projection along the b axis; small circles denote hydrogen atoms.

Infrared spectra were run as Nujol mulls or KBr disc on Perkin-Elmer 137 or 297 spectrometers. The mass spectrum was obtained on an MS-902 spectrometer at the Research Triangle Institute Centre for Mass Spectrometry, Research Triangle Park, North Carolina. Elemental analyses were by Galbraith Laboratories, Inc., Knoxville, Tennessee.

Sodium cyanide, hexane, ammonia, and anhydrous diethyl ether were obtained commercially and used without further purification. The complex NMe$_3$BH$_2$I was prepared by use of published procedures (see M. P. Brown et al, J. Chem. Soc. (A), 1970, p. 410) and sublimed before use.

Preparation of [Na{NH$_3$.BH$_2$(CN)}$_6$]I.

Sodium cyanide (20.5 g, 0.42 mol) and NMe$_3$BH$_2$I (82 g, 0.41 mol) were placed in a flask (500 cm$^3$) which was equipped with a magnetic stirring bar and attached to a standard vacuum system. Following evacuation of the flask, NH$_3$ (ca. 250 cm$^3$) was condensed into it at $-78°$ C., with the aid of a coolant bath. The mixture was then stirred and allowed to warm slowly by removing the coolant bath from the flask with excess of NH$_3$ being allowed to escape through a mercury bubbler. After stirring overnight, the remaining NH$_3$ was removed in vacuo leaving a white solid which was stirred with three separate portions (25–50 cm$^3$) of anhydrous diethyl ether; the decantates were combined and filtered under nitrogen. Hexane was then added slowly with gentle swirling until faint cloudiness became evident, at which point the solution was allowed to stand for 1–3 d. The product was collected by filtration and dried in vacuo to give [Na{NH$_3$.BH$_2$(CN)}$_6$]I (8.94 g, 27.0%), m.p. 94°–95.5° C. When excess of hexane was added beyond the point of first visible cloudiness, some precipitation of an unidentified powder-like substance of high melting point ($>140°$ C.) was observed. When this occurred, all the solvents were removed in vacuo and the residue was subjected to the above procedure. The mass spectrum of the complex contained a peak at m/e 55 (relative intensity 18.1) which is assignable to [BCH$_4$N$_2$]$^+$, the [M$-$1]$^+$ ion of NH$_3$BH$_2$(CN). The i.r. spectrum consisted of absorptions at 3 280s,br, 3 150s,br, 2 760w, 2 405s, 2 345m (sh), 2 260m, 2 195m, 2 110w, 1 770w,br, 1 635w, 1 575m, 1 385s, 1 175m, 1 130s, 1 070m, 905s, 815m, and 710m cm$^{-1}$.

(Found: C, 15.05; H, 6.35; B, 12.7; N, 34.9. Calc. for C$_6$H$_{30}$B$_6$IN$_{12}$Na: C, 14.85; H, 6.20; B, 13.35; N, 34.65%).

When the complex was heated to 105° C. for 1 h there was no change in the i.r. spectrum or m.p. An aqueous solution of the complex (in an evacuated flask) was stable towards evolution of H$_2$ over a period of at least 2 d.

Acid Hydrolysis of [Na{NH$_3$.BH$_2$(CN)}$_6$]I.

When the complex (0.096 g, 0.198 mmol) was mixed with excess of concentrated HCl in an evacuated flask on a vacuum system, hydrogen evolution was very slow. The evolved hydrogen was transferred by a Toepler pump and measured in a gas burette (Found: 0.052 mmol, 2.18% after 1 h; 0.196 mmol, 8.24% after 70 h. Calc. based on 12 hydridic hydrogen atoms per mol of complex: 2.38 mmol).

Basic Hydrolysis of [Na{NH$_3$.BH$_2$(CN)}$_6$]I.

When the complex (0.150 g, 0.309 mmol) was allowed to react with excess of 1 N NaOH in an evacuated flask, more rapid hydrogen evolution was observed (Found: 3.62 mmol, 97.6% after 45 min; 3.68 mmol, 99.2% after 20 h. Calc. based on 12 hydridic hydrogen atoms per mol of complex: 3.71 mmol).

Crystal Data

C$_6$H$_{30}$B$_6$IN$_{12}$Na, M=485.2, Rhombohedral, a=b=c=8.506(4) Å, $\alpha=\beta=\gamma=82.54(5)°$, U=601.0 Å$^3$, D$_m$ (flotation)=1.34 g cm$^{-3}$, Z=1, D$_c$=1.340 g cm$^{-3}$, F(000)=244. Cu-K$\alpha$ radiation, $\lambda$=1.541 8 Å; $\mu$(Cu-K$\alpha$)=110 cm$^{-1}$. Space group R$\bar{3}$(C$_{3i}^2$) by structure solution and refinement.

Crystallographic Measurements

Preliminary unit-cell dimensions and space-group information were obtained from oscillation and Weissenberg photographs taken with Cu-K$\alpha$ radiation and from precession photographs taken with Mo-K$\alpha$ ($\lambda$0.710 7 Å) radiation. For intensity measurements, a crystal of dimensions ca. 0.24$\times$0.24$\times$0.24 mm, sealed inside a thin-walled glass capillary to prevent deterioration, was orientated on a Enraf-Nonius CAD-3 automated diffractometer (nickel-filtered Cu-K$\alpha$ radiation; 3° take-off angle). Refined unit-cell parameters were derived from least-squares treatment of the $\theta,\chi$, and $\phi$ angles for 40 accurately centred high-order reflections widely separated in reciprocal space. The effects of absorption were determined from the $\phi$ dependence of the 3$\bar{3}$3 reflection measured at $\chi$90°. Intensities for all the accessible reflections to θ67° were recorded by the θ–2θ scanning procedure with scan widths $(1.00+0.50 \tan \theta)°$. Stationary background measurements were made at each end of the scan range for half the duration of the scan period. Instrument and crystal stability, monitored throughout by remeasuring the intensity of the 202 reflection after each batch of 99 measurements, showed only insignificant random variation. From a total of 2 158 measurements, the 1 885 reflections for which $I > 2.0\sigma(I)$, where $\sigma^2(I) = $ (scan count + total background count), were corrected for absorption, Lorentz, and polarization effects, and equivalent forms then merged into a unique set of 1 293 observed reflections which were used for the structure refinement.

Structure Analysis

The measured crystal density when considered in conjunction with the mass-spectral data and elemental analysis suggested the presence of an iodine atom. Since the actual nature of the complex was unknown, the structural problem was treated initially as belonging to space group P1 with the iodide ion placed at the origin of the unit cell. Evaluation of three-dimensional Patterson and Iodine-phased (R 0.31) Fourier syntheses revealed a large peak at $\frac{1}{2}, \frac{1}{2}, \frac{1}{2}$ which was ascribed to a sodium ion since this was present in the synthetic procedure and could accord with the anticipated high site symmetry. A subsequent difference-Fourier synthesis (R 0.29) yielded positions for three pairs of centrosymmetrically related N-B-C-N units. After refinement of atomic positional and isotropic thermal parameters to R 0.087 by several cycles of full-matrix least-squares calculations, inspection of the co-ordinates molecules revealed that they conformed to the six-fold general positions of space group $R\bar{3}$, and all the subsequent calculations were performed by use of the appropriate equivalent positions.

Hydrogen-atom positions were then located in a difference-Fourier synthesis and, with their contributions included in the next structure-factor calculation, R decreased to 0.070. Several further rounds of least-squares calculations, during which hydrogen-atom positional and isotropic thermal parameters, boron, carbon, and nitrogen positional and anisotropic thermal parameters, and sodium and iodine isotropic thermal parameters were varied, brought the refinement to convergence at R 0.063. Final values for the atomic positional parameters are in Table 1.

Table 1

Fractional atomic co-ordinates ($\times 10^4$, H, $\times 10^3$) with estimated standard deviations in parentheses

| Atom | x | y | z |
|---|---|---|---|
| Na | 5 000(—) | 5 000(—) | 5 000(—) |
| I | 0(—) | 0(—) | 0(—) |
| N(1) | 1 978(5) | −1 050(5) | 6 095(5) |
| B(2) | 1 994(8) | 640(7) | 5 074(8) |
| C(3) | 3 441(6) | 1 475(6) | 5 434(6) |
| N(4) | 4 443(6) | 2 177(5) | 5 664(6) |
| H(1A) | 107(11) | −176(10) | 581(11) |
| H(1B) | 180(9) | −111(9) | 719(9) |
| H(1C) | 293(8) | −163(8) | 591(8) |
| H(2A) | 93(6) | 147(6) | 539(6) |
| H(2B) | 215(11) | 45(11) | 373(12) |

A list of observed and calculated structure amplitudes and thermal parameters is in Supplementary Publication No. SUP 22126 (11 pp.). For details, see Notices to Authors No. 7, *J. C. S. Dalton*, 1976, Index issue.

For all the structure—factor calculations, scattering factors for ionic sodium and iodine (corrected for the real part of anomalous dispersion—see *International Tables for X-Ray Crystallography*, Kynoch Press, Birmingham, 1968, vol. 3), and for neutral boron, carbon, and nitrogen, were taken from D. T. Cromer et al, *Acta Cryst.*, 1965, vol. 18, p. 104. Scattering factors for hydrogen were taken from R. F. Stewart et al, *J. Chem. Phys.*, 1965, vol. 42, p. 3175. In the least-squares calculations, $\Sigma \omega \Delta^2$ was minimized, with weights $\omega$ being assigned according to the scheme $\omega^{\frac{1}{2}} = 1$ for $|F_o| \leq 32.0$ and $\omega^{\frac{1}{2}} = 32.0/|F_o|$ for $|F_o| < 32.0$; no systematic dependence was revealed when $\Sigma \omega \Delta^2$ was analysed in ranges of $|F_o|$. Calculations were made on an I.B.M. 370/165 computer at the Triangle Universities Computation Centre, North Carolina, using locally written programs.

RESULTS AND DISCUSSION

The X-ray analysis establishes that the crystalline reaction product is the 6:1 ammonia-cyanoborane complex with sodium iodide, $[Na\{NH_3 \cdot BH_2(CN)\}_6]I$. The atom-numbering scheme and packing arrangement in the crystal are shown in FIG. 1. Interatomic distances and angles are in Table 2.

The iodide ions are located at the corners of the rhombohedral unit cell (Wyckoff position 1a, $\bar{3}$ site symmetry) and the sodium ions are at $\frac{1}{2}, \frac{1}{2}, \frac{1}{2}$ (Wyckoff position, 1b, $\bar{3}$ site symmetry). Interposed between these ions are the $NH_3 \cdot BH_2(CN)$ units which occupy the six-fold general positions of space group $R\bar{3}$ and are consequently distributed in a regular octahedral arrangement around both the sodium and iodide ions.

The Na$^+$ ... N(cyano) distance [2.487(4) Å] in the complex is close to the means of 2.492 Å in sodium α, α, α′, α′-tetracyanoquino-dimethanide [range 2.418(3)–2.565(4) Å, see M. Konno et al, *Acta Cryst*, 1974, B 30, p. 1294] and 2.512 Å in $Na[C(CN)_3]$ [2.374(3)–2.613(3) Å, see P. Andersen et al, *Acta Chem Scand.*, 1967, vol. 21, p. 1530.].

Associated with these ranges of distances characterizing distorted octahedral arrangements around Na$^+$, in each of the latter complexes is a corresponding range (107.4°–166.9°) of Na$^+$ ... N—C angles.

Table 2

Interatomic distances (Å) and angles (°) with estimated standard deviations in parentheses (a) Distances

| | | | |
|---|---|---|---|
| N(1)—B(2) | 1.581(8) | N(1)—H(1C) | 0.89(7) |
| B(2)—C(3) | 1.579(8) | B(2)—H(2A) | 1.10(5) |
| C(3)—N(4) | 1.152(7) | B(2)—H(2B) | 1.16(10) |
| N(1)—H(1A) | 1.11(9) | N(4) ... Na | 2.487(4) |
| N(1)—H(1B) | 0.92(8) | | |

(b) Angles

| | | | |
|---|---|---|---|
| N(1)—B(2)—C(3) | 109.7(5) | C(3)—N(4) ... Na | 134.2(4) |
| B(2)—C(3)—N(4) | 175.8(5) | | |

Figure 2:
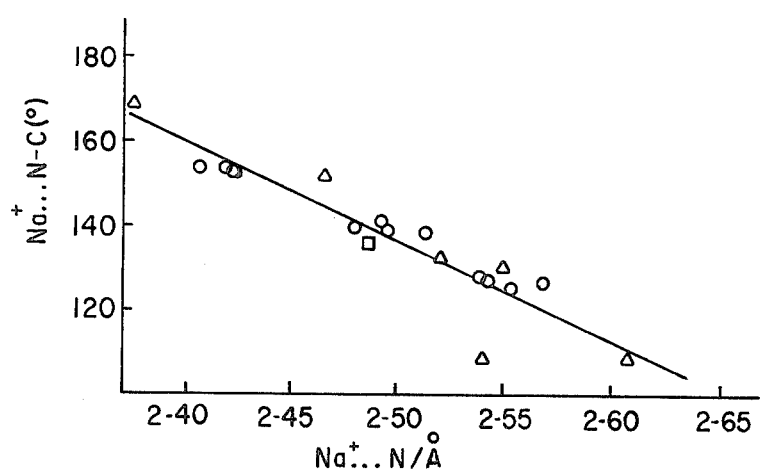
FIG. 2 is a plot of the variation of Na$^+$ ... N-C angle with Na$^+$ ... N distance for: (O) sodium $\alpha$, $\alpha$, $\alpha'$, $\alpha'$-tetracyanoquino dimethanide; ($\Delta$) sodium tricyanomethanide; ($\square$) our complex.

A plot of these angles against the Na$^+$ ... N distances shows that they vary in a systematic manner (see FIG. 2) which strongly suggests that the value assumed by the Na$^+$ ... N—C angle is not merely a consequence of random crystal-packing forces but may be dependent on the charge density at nitrogen; the shorter is the Na$^+$ ... N distance the closer to 180° is the Na$^+$ ... N—C angle, and the longer is the Na$^+$ ... N distance the more bent is the Na$^+$ ... N—C angle. (A complete list of the data plotted is available in SUP 22126.) Substitution of the Na⁺ ... N distance from the present study into the derived least-squares equation through the plotted values [θ=al+b, where θ (°) is the Na⁺ ... N—C angle, a=−232.1° A⁻¹, b=715.7°, and l(Å) is the Na⁺ ... N distance] yields a calculated value for the Na⁺ ... N—C angle of 138.4(1)° which accords well with the experimentally observed value of 134.2(4)°. Since the Na⁺ ... N—C angle found in the title complex lies closer to 120 than to 180°, it appears that canonical form B makes a greater contribution than A. On the other hand, the C(3)—N(4) distance [1.152(7) Å] is in excellent agreement with the normal C≡N value [1.158(2) Å] and consequently shows no evidence of any elongation which might be expected to accompany the change in hybridization associated with form B. This observation may be rationalized if the expected elongation from this source is counterbalanced by increased ionic attraction between the carbon and nitrogen atoms in zwitterionic form B, thereby resulting in a constancy of bond length in forms A and B.

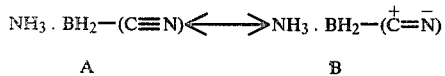

Alternatively, in form B the nitrogen atom may be viewed as having a non-equivalent set of sp²—hybridized orbitals of which one with an above-average amount of s character is directed towards the carbon atom.

Bond lengths involving the boron atom are not unusual. The B(2)-C(3) distance [1.579(8) Å] is close to that of 1.56 Å in [BH₃(CN)] (K. M. Melmed et al, *J. Amer. Chem. Soc.*, 1974, vol. 96, p. 69) and [BH₂-(CN)]₆ (A. T. McPhail et al, *J. C. S. Dalton*, 1975, p. 1784). The B(2)—N(1) bond length [1.581(8) Å] does not differ significantly from those found for other related compounds [1.578(7)-1.581(3) Å]. See D. S. Kendall et al, *Inorg. Chem.*, 1973, vol. 12, p. 2920; C. E. Nordman et al, *J. Amer. Chem. Soc.*, 1959, Vol. 81, p. 3538; and R. Lewin et al, *J. Chem. Phys.*, 1963, Vol. 39, p. 1532. Since it has been demonstrated that B—N distances provide some indication of donor and acceptor strengths (see Kendall et al, supra, and W. N. Lipscomb et al, *Adv. Chem. Ser.*, 1964, vol. 42, p. 312), the close correspondence between the bond length in the complex and that of 1.578(8)Å in NH₃.BH₂—(NCS) indicates that BH₂—(CN) must have an acceptor strength similar to BH₂—(NCS). The mean B—H distance (1.13 Å) is also in good accord with accepted values (*International Tables for X-Ray Crystallography*, Kynoch Press, Birmingham, 1968, vol. 3).

The mean N—H distance (0.97 Å) is normal. The shortest separation involving the NH₃ group and the iodide ion is H (1B) ... I⁻ at 2.87 Å with an associated N(1)—H(1B) ... I⁻ angle of 149.1°. This distance is significantly less than the sum of the van der Walls radii (3.15 Å). See L. Pauling, *The Nature of the Chemical Bond*, 3d ed., Cornell University Press, ithaca, N.Y., 1960, and W. H. Baur, *Acta Cryst.*, 1972, B28, p. 1456. In all probability, this represents a weak hydrogen-bonded interaction.

UTILITY

Evidence indicates that the complex of this invention is a valuable antiarthritic agent, since it completely inhibits bacteria-inducted chronic arthritis in rats with no evidence of toxic effects. More specifically, chronic anthritis was induced in Sprague-Dawley male rats by the method of B. H. Waksman et al, *J. Immunol.*, vol. 85, p. 403 (1960). When the complex was administered to these rats at 2.5 mg/kg body weight/day I. P., it caused 100% inhibition of the induced arthritis.

Furthermore, analgesic activity was determined by the method of inhibition of writhing reflex as described by R. Vinegar et al, *European J. Pharmacol.*, vol. 37, p. 23 (1976). When administered to mice at 20 mg/kg I. P., the complex was 88% inhibiting.

Finally, anti-inflammatory activity was tested using the following procedures: (1) C. A. Winter et al, *Proc. Soc. Exp. Biol & Med.*, vol. 111, p. 544 (1962); and (2) A. D. Roszkowski et al, *J. Pharmacol. Exp. Ther.*, vol. 179, p. 114 (1971). By using the method of dosing described in Winter et al, the complex was administered at a dose of 10 mg/kg×2 I. P. to Sprague-Dawley male rats. By using the procedure for determining anti-inflammatory activity as described by Winter et al and modified by Roszkowski et al, the complex was found to be 43% inhibiting.

The LD₅₀ for the complex was determined according to the method of J. T. Leitchfield et al, *J. Pharmacol. Exp. Ther.*, vol. 96, p. 99 (1949). The LD₅₀ in CF₁ male mice weighing approximately 30 grams was determined to be 100 mg/kg.

We claim:
1. [Na{NH₃.BH₂(CN)}₆]I
2. The method of treating an animal which has arthritis, inflammation, or pain by administering to said animal an effective amount of [Na{NH₃.BH₂(CN)}₆]I.
3. The method of claim 2 wherein the animal has arthritis.
4. The method of claim 2 wherein the animal has inflammation.
5. The method of claim 2 wherein the animal has pain.